United States Patent
Fiedler et al.

(10) Patent No.: US 10,045,853 B2
(45) Date of Patent: Aug. 14, 2018

(54) ARTIFICIAL KNEE JOINT

(71) Applicant: LIMACORPORATE S.P.A., San Daniele del Friuli (IT)

(72) Inventors: Christoph Fiedler, Udine (IT); Andrea Camera, Calice Ligure (IT); Ivana Barbanti, San Daniele del Friuli (IT); Nicola Ursino, Loano (IT); Bruno Violante, Cava dei Tirreni (IT); André Ferreira, Caluire (FR)

(73) Assignee: LIMACORPORATE S.P.A., San Daniele del Friuli (IT)

( * ) Notice: Subject to any disclaimer, the term of this patent is extended or adjusted under 35 U.S.C. 154(b) by 0 days.

(21) Appl. No.: 15/117,358

(22) PCT Filed: Feb. 10, 2015

(86) PCT No.: PCT/IB2015/050997
§ 371 (c)(1),
(2) Date: Aug. 8, 2016

(87) PCT Pub. No.: WO2015/118517
PCT Pub. Date: Aug. 13, 2015

(65) Prior Publication Data
US 2017/0007415 A1    Jan. 12, 2017

(30) Foreign Application Priority Data

Feb. 10, 2014   (IT) .............................. UD2014A0023

(51) Int. Cl.
*A61F 2/38* (2006.01)

(52) U.S. Cl.
CPC ............ *A61F 2/3886* (2013.01); *A61F 2/389* (2013.01); *A61F 2/3859* (2013.01)

(58) Field of Classification Search
CPC ...... A61F 2/3859; A61F 2/389; A61F 2/3886; A61F 2/38; A61F 2002/30604; A61F 2002/30116; A61F 2002/3863
See application file for complete search history.

(56) References Cited

U.S. PATENT DOCUMENTS

| 5,549,686 A | 8/1996 | Johnson et al. |
| 6,013,103 A | 1/2000 | Kaufman et al. |

(Continued)

FOREIGN PATENT DOCUMENTS

| EP | 0941719 A2 | 9/1999 |
| EP | 1591082 A2 | 11/2005 |

OTHER PUBLICATIONS

International Search Report and Written Opinion dated May 4, 2015 in International Application No. PCT/IB2015/050997.

*Primary Examiner* — Ann Schillinger
(74) *Attorney, Agent, or Firm* — Panitch Schwarze Belisario & Nadel LLP

(57) ABSTRACT

An artificial knee joint includes a femoral component (11), provided with a medial condyle (13), a lateral condyle (14) and a front flange (50). The medial condyle (13) and the lateral condyle (14) are joined together in proximity with the rear end of the intercondyle groove (19) by a femoral cam (17), and separated by the intercondyle groove (19) in the remaining part of their extension. A tibial component includes a tibial plate and a tibial insert (12). The tibial insert (12) is configured to support the medial condyle (13), and the lateral condyle (14), and is provided with a tibial post (18). The femoral cam (17) is asymmetrical and comprises a distal surface (20) shaped like a drum which articulates with the tibial post (18).

4 Claims, 5 Drawing Sheets

(56) References Cited

U.S. PATENT DOCUMENTS

| | | |
|---|---|---|
| 2007/0135925 A1 | 6/2007 | Walker |
| 2009/0319048 A1* | 12/2009 | Shah .................... A61F 2/38 |
| | | 623/20.29 |
| 2010/0161067 A1 | 6/2010 | Saleh et al. |
| 2012/0143342 A1 | 6/2012 | Mihalko et al. |
| 2013/0204380 A1 | 8/2013 | Mouillet et al. |

* cited by examiner

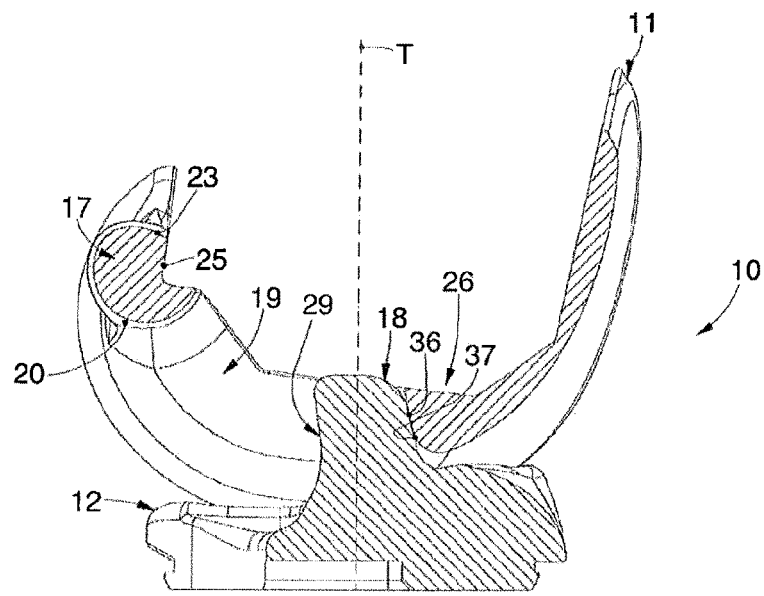
fig. 1
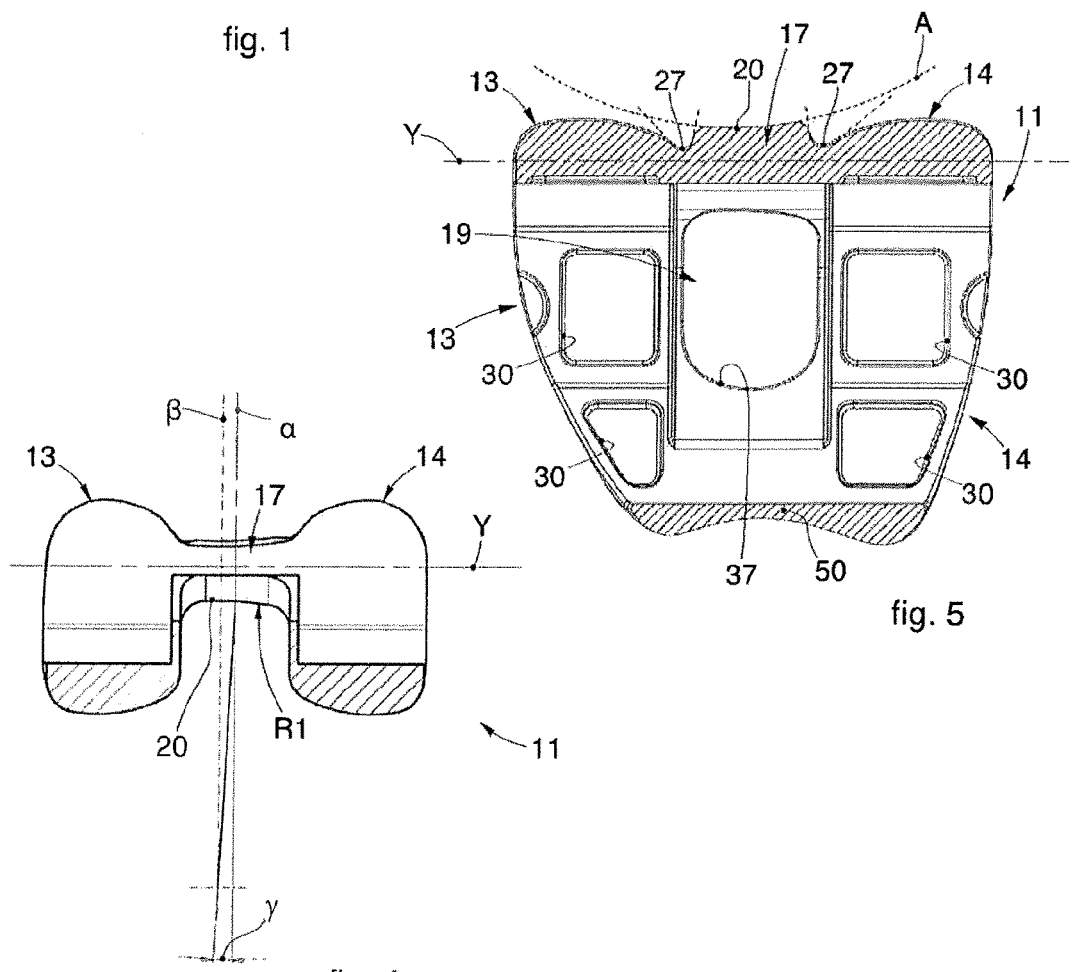
fig. 4
fig. 5

ARTIFICIAL KNEE JOINT

CROSS-REFERENCE TO RELATED APPLICATION

This application is a Section 371 of International Application No. PCT/IB2015/050997, filed Feb. 10, 2015, which was published in the English language on Aug. 13, 2015, under International Publication No. WO 2015/118517 A1, and the disclosure of which is incorporated herein by reference.

FIELD OF THE INVENTION

The present invention concerns an artificial knee joint usable to replace a biological knee joint.

BACKGROUND OF THE INVENTION

An artificial knee joint, or knee prosthesis, is used to replace a biological knee if the latter is subjected for example to primary or secondary arthrosis, due to a trauma or caused by infections, post-traumatic arthrosis, rheumatoid arthritis, inflammatory arthritis, meniscectomy, osteo-necrosis, or bone tumors, or again if the biological knee is subjected to particularly serious traumas or other similar problems.

Known knee prostheses typically comprise a femoral component, which is attached to the distal end of the femur, and a tibial component, which is attached to the proximal end of the tibia.

The femoral component, as its main components, normally has a medial condyle, a lateral condyle, partly separated from each other by an intercondyle groove, and a front flange.

The tibial component normally comprises a tibial plate, which is attached during use to the proximal end of the tibia, and an insert, which comprises a medial articulation surface and a lateral articulation surface, on which respectively the medial condyle and the lateral condyle of the femoral component articulate during use.

The condyles and the articulation surfaces are all in all configured to reproduce a movement similar to that of a healthy biological knee.

More specifically, the femoral component and the tibial component are normally configured to reduce as much as possible the probability that incorrect movements occur due to anomalous translations in the front, rear, medial or lateral directions, and rotations.

In surgical operations that use a total knee prosthetic implant, the anterior cruciate ligament is generally removed.

Instead, the posterior cruciate ligament is removed if its functionality is deemed compromised or if the functionality is totally non-existent, for example due to a pathological evolution.

The presence of the two collateral ligaments, that is, the medial and lateral ligaments, is necessary for the overall stability of the artificial joint.

When the anterior and posterior cruciate ligaments have been removed and at the same time a good functionality of the collateral ligaments is maintained, it is necessary to use a prosthetic configuration that allows to restore the original mechanical stability.

This configuration commonly provides, in some known prosthesis solutions, a tibial post, or simply post, with a proximal prominence, provided on the tibial insert in its central zone, that is, positioned between the medial and lateral articulation surfaces of the tibial insert itself.

The tibial post is inserted inside the intercondyle groove of the femoral component when the prosthesis is implanted.

In some known prosthesis solutions, the post also interferes with a femoral cam, or simply cam, located in proximity to the rear end of the intercondyle groove, or in a position opposite the front flange, to restore the functionality of the posterior cruciate ligament that has been removed.

The post and the cam usually articulate for a reduced portion of the flexion of the joint.

During the flexion of the leg, a rotation movement also occurs of the biological knee with respect to the tibial axis toward the outside, and this rotation also occurs in a prosthesized knee provided with an artificial joint.

The amplitude of such rotations depends in particular on specific conditions of the individual patient. Therefore, it is not recommended to facilitate the external rotation through contact between post and cam for a fixed degree of rotation, but it is advantageous to provide an optimized geometry for post and cam for a wider range of external rotation.

Therefore, for this reason, the areas of post and cam intended to enter into reciprocal contact during rotation are designed not congruently, through an asymmetrical design, so as to allow a sufficiently wide range of variability and to supply contact for different degrees of external rotation.

The prior art documents EP 1 591 082 B1, US 2012/0143342, US 2007135925, U.S. Pat. No. 6,013,103, EP 0941719 A, U.S. Pat. No. 5,549,686, and the scientific article by Cates et al. "In Vivo Comparison of Knee Kinematics for Subjects Having Either a Posterior Stabilized or Cruciate Retaining High-Flexion Total Knee Arthoplasty", describe solutions for articular knee prostheses that are proposed at least partly to solve the problems deriving from external rotation during flexion.

The solutions proposed in these prior art documents are not completely satisfactory however, because in some forms of embodiment the cam has a symmetrical profile that does not allow a suitable same-shape coupling of the cam and post during external rotation.

Another disadvantage of some known forms of embodiment is that the external rotation is forced by the contact between the femoral cam and the tibial post during the flexion movement, which makes this movement less natural and at the same time leads to an increase in wear, of both the cam and the post.

The increase in wear can also lead to a reduction in the life of the knee prosthesis.

In some known forms of embodiment, the tibial insert has an asymmetrical contact surface of the post, intended to enter into contact with the cam.

This asymmetry does not allow to exchange the right and left femoral component using a single tibial insert.

It is therefore a purpose of the present invention to obtain an artificial knee joint that facilitates the natural movements of the leg, completely reproducing the natural kinematics of a healthy knee.

Another purpose of the present invention is to obtain an artificial knee joint that reduces the stresses deriving from the interaction between femoral component and tibial component.

The Applicant has devised, tested and embodied the present invention to overcome the shortcomings of the state of the articulation and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, an artificial knee joint according to the present invention comprises a femoral component, able to be attached to the distal end of a femur; the femoral component comprises at least a medial condyle and a lateral condyle. The joint also comprises a tibial component able to be attached to the proximal end of the tibia; said tibial component comprises a tibial plate and a tibial insert.

The tibial insert is configured to support the medial condyle and the lateral condyle, allowing them to articulate, through respectively a medial articulation surface and a lateral articulation surface.

The tibial insert is provided centrally with a symmetrical post, disposed longitudinally between the two articulation surfaces, so that the post is positioned inside the femoral intercondyle groove, defined by the medial condyle and the lateral condyle; the femoral intercondyle groove extends from the rear end of the femoral component to a front flange.

The femoral component is also provided with a cam, hereafter referred to as femoral cam, disposed in proximity to the rear portion of the intercondyle groove that comes into contact with the rear surface of the post during a part of the flexion of the joint.

The tibial post and the femoral cam are shaped so that the femoral component facilitates the external rotation when the femoral cam comes into contact with the post.

In some forms of embodiment, the femoral cam has a development along an axis perpendicular to the central femoral plane. Furthermore, the femoral cam can be provided with a distal surface defined by the rotation, with respect to said axis, of an arc of a circumference.

In another preferential formulation, the post is symmetrical with respect to a central plane of the tibial insert.

This symmetry allows to interchange the tibial component for different femoral components for the right leg or femoral components for the left leg.

This is possible because the conformation of the femoral component itself, and in particular of the femoral cam, is optimized for a particular leg.

According to another characteristic of the present invention, the rear surface of the post is not congruent with respect to the contact surface of the cam, so that the cam and the post allow the external rotation during flexion and supply a central contact area.

The artificial knee joint made with these characteristics reproduces the physiological movements of a biological knee in a particularly natural way.

Moreover, this configuration allows to reduce stresses to which the femoral component and the tibial component of known artificial knee joints are normally subjected.

BRIEF DESCRIPTION OF THE DRAWINGS

These and other characteristics of the present invention will become apparent from the following description of some forms of embodiment, given as a non-restrictive example with reference to the attached drawings wherein:

FIG. 1 is a lateral section view of the central plane of one form of embodiment of an artificial knee joint in hyperextension according to the present invention;

FIG. 4 is a central section view parallel to the front plane of a femoral component of an artificial knee joint according to the present invention;

FIG. 5 is another section view from above, passing through the center of the cam of a femoral component according to one form of embodiment of the present invention;

Figure 2:
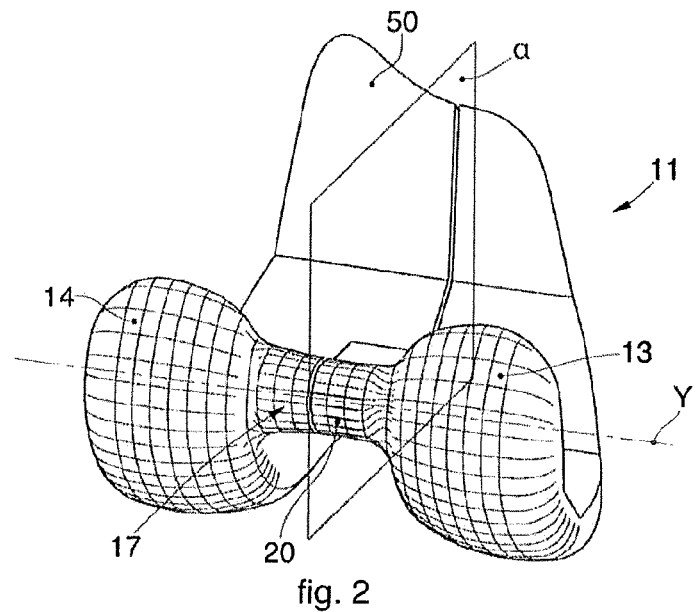
FIG. 2 is a perspective view of a femoral component according to the present invention.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF SOME FORMS OF EMBODIMENT

We shall now refer in detail to the various forms of embodiment of the invention, of which one or more examples are shown in the attached drawings.

Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

Figure 3:
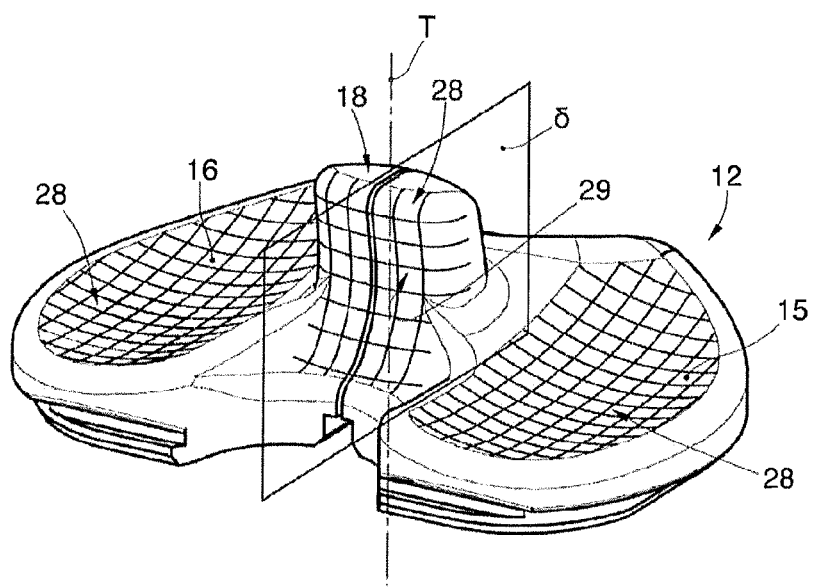
FIG. 3 is a perspective view of a tibial component according to the present invention.

FIGS. 1-3 are used to describe forms of embodiment of an artificial knee joint or knee prosthesis, hereafter indicated as artificial joint 10.

The artificial joint 10 comprises a femoral component 11, suitable to be attached to the distal end of a femur (not shown in the drawings), and a tibial insert 12, suitable to be attached by means of a tibial plate (not shown, as it is the conventional type and not relevant for the purposes of the invention) to the proximal end of a tibia (also not shown in the drawings).

The tibial insert 12 and the tibial plate together comprise a tibial component of the artificial joint 10.

The femoral component 11 comprises a medial condyle 13 and a lateral condyle 14 separated by an intercondyle groove 19 (FIG. 5) and joined by a front flange 50.

Both the condyles 13, 14 and the front flange 50 have a curved shape and the femoral component 11 generally delineates in its internal part an internal concavity 26 that is occupied during use by the femur, suitably cut and adapted.

The femoral component 11 also comprises a femoral cam, also called simply cam 17.

The cam 17 has a development along an axis Y, easily visible in FIGS. 3, 4 and 5, and is provided perpendicular to the central femoral plane and in proximity to the rear end of the intercondyle groove 19, that is, in a position opposite to the front flange 50.

According to forms of embodiment described using FIG. 5, the condyles 13 and 14 can have lowered surfaces, also called surface depressions 30, in their internal part, in order to contain the acrylic cement needed to attach them to the bone.

Figure 9:
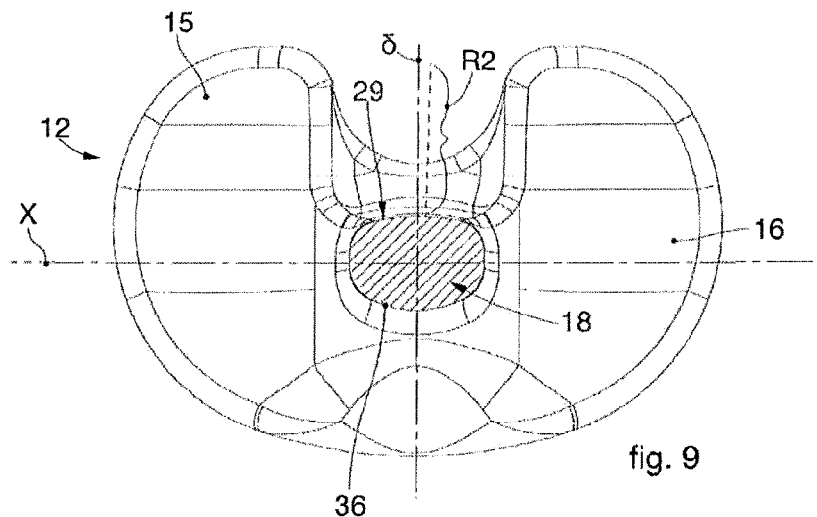
FIG. 9 is a view from above of a section of the tibial insert that passes through the post according to one form of embodiment of an artificial knee joint of the present invention.

In some forms of embodiment, the tibial insert 12 has a medial articulation surface 15 and a lateral articulation surface 16 that in use respectively support the medial condyle 13 and the lateral condyle 14 (FIGS. 3 and 9).

The tibial insert 12 comprises a tibial post 18, also hereafter simply post 18, able to be positioned during use in the intercondyle groove 19 and in particular made to interfere with the cam 17.

The medial articulation surface 15, the lateral articulation surface 16 and the rear surface 29 of the post 18 together achieve the tibial articulation surface 28 with the femoral component 11.

The tibial insert 12 also comprises a base surface 42, suitable to interface with the tibial plate mentioned above, in a substantially known manner.

The distal surface 20 of the cam 17 is configured to enter into contact with the post 18 for determinate angles of flexion of the leg.

Figure 6:
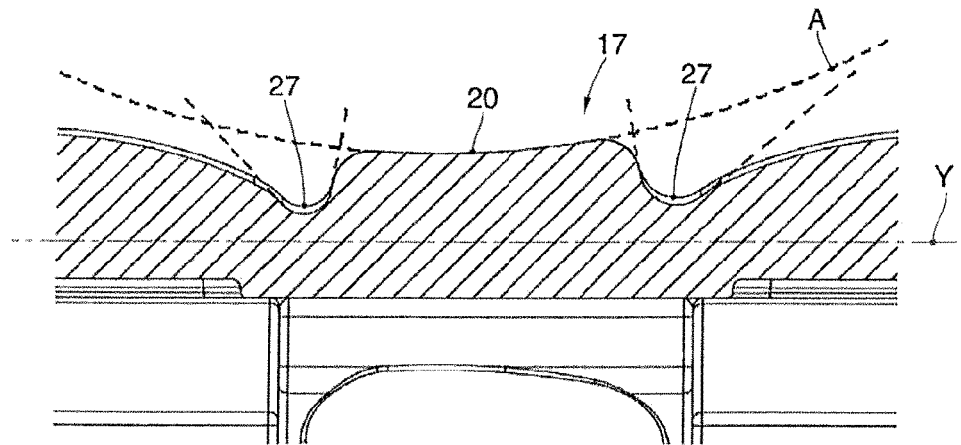
FIG. 6 is an enlarged detail of the femoral component in FIG. 5.

The distal surface 20 is drum-shaped, the center of which has a concavity defined by an arc A, as shown in FIGS. 5 and 6, with a radius R1 (easily visible in FIG. 2).

The drum-shape is defined in particular by the rotation of the arc A of a circumference around the central axis Y of the cam 17, perpendicular to the central femoral plane α.

The center of the arc A lies on a medial plane β, parallel to but not coincident with the central femoral plane α, and at a distance defined by the angle γ of the line between the point of intersection of the arc A with the central femoral plane α and the center of the arc A with respect to the central femoral plane α itself.

In possible implementations, the angle γ can be comprised between 1 and 6°, preferably between 2° and 5°, more preferably about 3°.

In particular, the angle γ thus defined also corresponds to the mean value of the angle of external rotation during the flexion of the leg.

By angle of external rotation we mean the angle created between the central axis Y of the femoral cam 17, projected on a plane perpendicular to a vertical axis T lying on the central tibial plane δ, and the medio-lateral axis X of the tibial insert 12. The medio-lateral axis X is therefore the axis perpendicular to the central tibial plane δ of the tibial insert 12.

The center of the distal surface 20 is nearer to the medial condyle 13 than to the lateral condyle 14, and this gives a maximum medial diameter that is less than the maximum lateral diameter of the distal surface 20.

Figure 7:
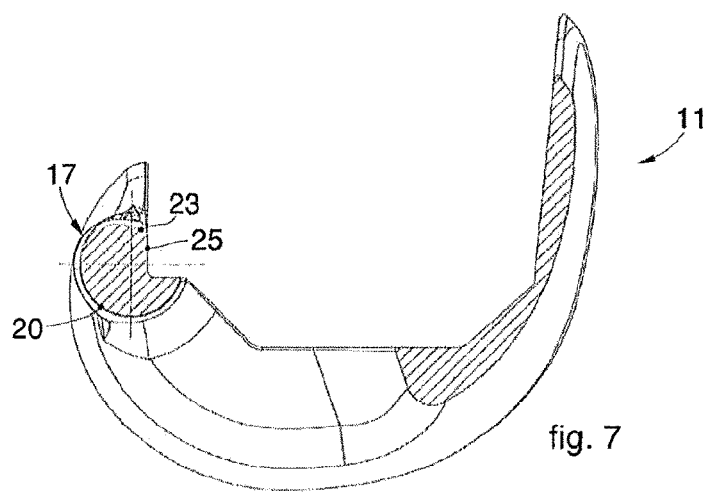
FIG. 7 is a lateral section view of the central plane of a femoral component according to the present invention.
Figure 8:
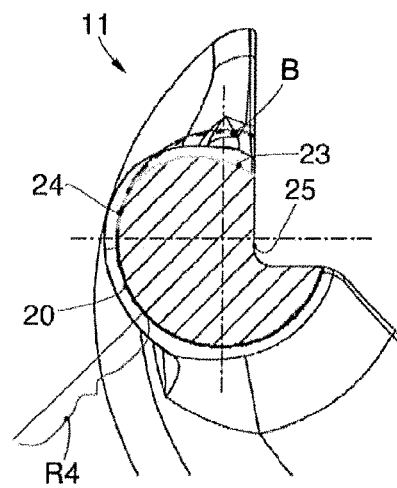
FIG. 8 is an enlarged detail of the femoral component in FIG. 7.

In the form of embodiment in FIGS. 7 and 8, the proximal surface 23 of the cam 17, not having particular functions to perform, can have a more arched curved surface in order to reduce the thickness of the cam 17.

In fact, the proximal surface 23 of the cam 17 does not come into contact with the post 18 for any angle of flexion of the femoral component 11 and tibial insert 12, and therefore is not functional.

In particular, as shown in FIGS. 7 and 8, the line of dashes B is the continuation of the revolution of the arc A around the central axis Y, which departs from a point 24 where the curve changes.

The proximal surface 23 is interrupted by an L-shaped connection surface 25, disposed toward the internal concavity 26 of the femoral component 11.

The position of the cam 17 in the rear portion of the femoral component 11 is advantageous in particular for the resistance of the post 18 and for the jump distance J.

The technical term "jump distance" means the minimum distance that the cam 17 of the femoral component 11 has to travel vertically so that it can pass the highest point of the post 18.

The jump distance J is therefore determined by the relative position of the cam 17 with respect to the intercondyle groove 19 and the height of the post 18 from the articulation surfaces 15 and 16.

In forms of embodiment according to FIGS. 5 and 6, there are two slits 27 on the rear-medial and rear-lateral part of the cam 17, to connect it respectively to the medial condyle 13 and the lateral condyle 14.

A continuation of the cam 17 without the slits 27 could influence the interaction between the condyles 13 and 14 and the tibial articulation surface 28.

The post 18 has a substantially rectangular shape in section, as shown in FIG. 9, and is symmetrical with respect to the central tibial plane S.

The rear surface 29 of the post 18 corresponds to the surface that during use enters into contact with the cam 17.

The rear surface 29 has an axial curve radius R2 that lies on a plane parallel to the base surface 42 of the tibial insert 12.

According to some forms of embodiment of the present invention, the radius R2 of the rear surface 29, lying on a plane parallel to the base plane 42 of the tibial insert 12 is substantially half a radius R1 of the arc A (FIG. 9 with respect to FIG. 4).

Figures 10, 11:
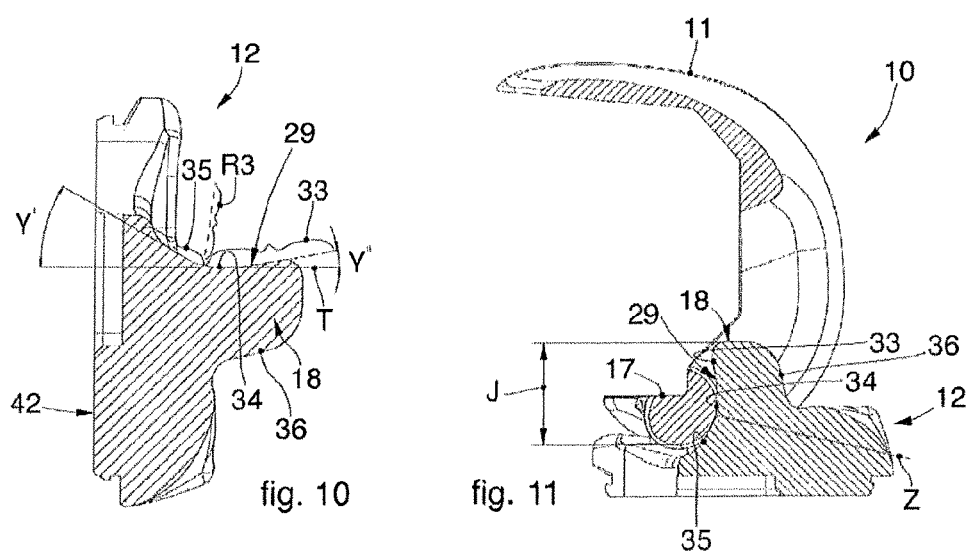
FIG. 10 is another lateral view in central section of a tibial insert according to one form of embodiment of the present invention.
FIG. 11 is a lateral view in central section of one form of embodiment of an artificial knee joint according to the present invention in a first functioning position at 900 of flexion.

In accordance with the lateral section view of the post 18, shown in FIG. 10, the rear surface 29 comprises a proximal portion 33, a central portion 34 and a distal portion 35.

The central portion 34 is made with a sagittal curve radius R3 which is bigger than the sagittal radius R4 of the distal surface 20 of the cam 17 (see FIG. 10 with respect to FIG. 8).

In possible implementations, the ratio between radius R3 and radius R4 is, by way of example, comprised between 10% and 50%, preferably between 25% and 35%.

According to some forms of embodiment, up to about 120° of the angle of flexion of the femur with respect to the tibia, the contact between post 18 and cam 17 is inside the central portion 34.

In forms of embodiment described using FIG. 10, the distal portion 35 is inclined by an angle γ' with respect to the vertical axis T.

In possible implementations, the angle γ' can be provided from about 25° to 55°, preferably from about 20° to 40°, more preferably about 30°.

In forms of embodiment according to the form of embodiment in FIG. 8, the proximal portion 33 is inclined by an angle γ" with respect to the vertical axis T.

In possible implementations, the angle γ" can be comprised in a range from about 3° to 20°, preferably from about 5° to 15°, more preferably about 10°.

Along the whole contact trajectory between post 18 and cam 17, the horizontal radius R2 is such as to create a similar contact configuration for the whole flexion movement.

As the point of contact between post 18 and cam 17 varies, for different angles of flexion and different angles of rotation of the leg, the radiuses R1, R2, R3, R4 remain constant.

In this way the contact surfaces of the femoral cam 17 and the post 18 are always similar.

According to some forms of embodiment, the post 18 provides at the front a surface, called front surface 36, which is substantially congruent with the front end 37 of the intercondyle groove 19.

In particular, the front surface 36 and the front end 37 are in contact during a possible hyperextension of the artificial joint 10, that is, when the tibia performs a movement opposite to flexion, reaching a maximum angle of hyperextension linked to the contact between said surfaces, as shown in FIG. 1.

The front surface 36 of the tibial insert 12 is constructed congruent with the front end 37 of the hyperextended femoral component 11. In this way any front weakening of the post 18 is prevented, in the event of any possible hyperextension.

In possible implementations, the maximum angle of hyperextension can be provided from about 3° to 9°, preferably from about 5° to 8°, more preferably about 7°.

The post 18 and the cam 17 are typically in contact only after a determinate angle of flexion of the femur with respect to the tibia has been passed.

In possible implementations, the angle of flexion at which the initial contact occurs between tibial post 18 and femoral cam 17 can be provided from about 60° to 110°, preferably from about 80° to 90°, more preferably about 85°.

The angle of flexion where the contact between tibial post 18 and femoral cam 17 starts is strictly dependent on the initial alignment between the femoral component 11 and the tibial insert 12, the situation of the ligaments and the movement occurring between femur and tibia.

In particular, if in addition to the flexion movement there are also rotations of the femur and tibia at the same time, the angle of flexion at which the initial contact occurs between tibial post 18 and femoral cam 17 can vary.

Figure 12:
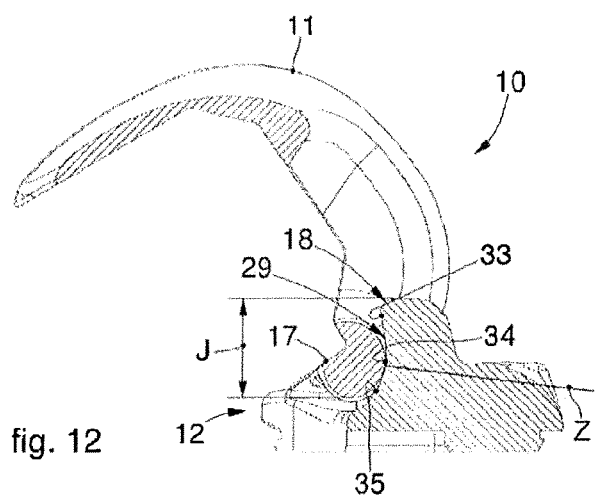
FIG. 12 is a lateral view in central section of one form of embodiment of an artificial knee joint according to the present invention in a second functioning position at 120° of flexion.

FIGS. 11 and 12 show respectively the situation where there is contact between post 18 and cam 17 for an angle of flexion between femur and tibia of 90° and 120°.

The point of contact of the post 18 with the cam 17 is provided for both situations in FIGS. 11 and 12, approximately in the central portion 34 of the rear surface 29 of the post 18.

In a point of contact between post 18 and cam 17, a direct force is exerted along an axis of application Z that has a downward and forward direction, as visible in both FIGS. 11 and 12.

According to some forms of embodiment, the post 18 and the cam 17 are made to have the greatest possible contact area between the distal surface 20 of the cam 17 and the rear surface 29 of the post 18, during the flexion of femur and tibia.

FIGS. 13-16 show, in particular, four situations at 90° of flexion, corresponding to different angles of external rotation of femur and tibia. FIGS. 13, 14, 15, 16 correspond respectively to angles of external rotation of 0°, 3°, 6° and 10°.

Figure 14:
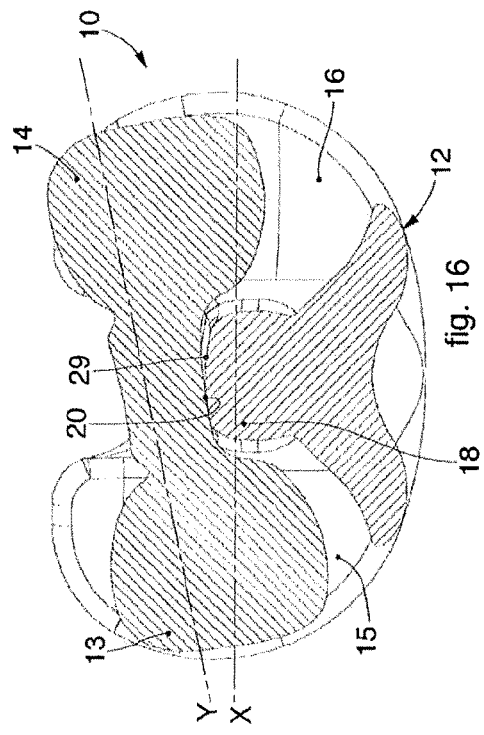
FIG. 14 is another section view from above of one form of embodiment of an artificial knee joint according to the present invention in a second functioning position at 90° of flexion with 3 degrees of external rotation.

As shown in FIG. 14, for an angle of external rotation of 30, the contact profile between the rear surface 29 of the post 18 and the distal surface 20 of the cam 17 is complementary in correspondence with a central contact point of both said surfaces.

Figure 13:
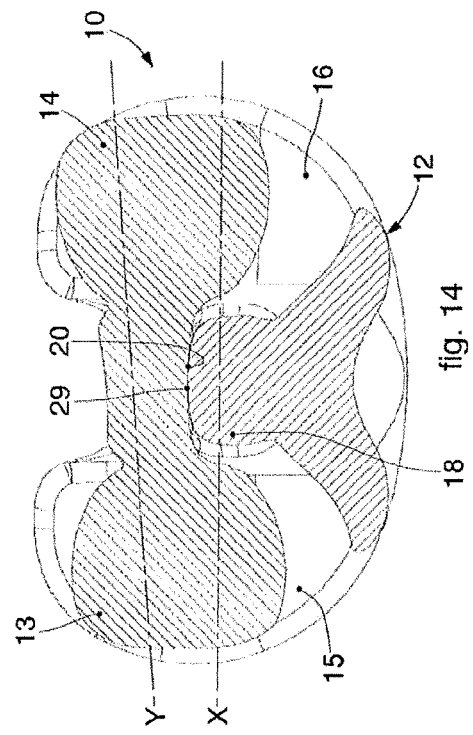
FIG. 13 is another section view from above of one form of embodiment of an artificial knee joint according to the present invention in a first functioning position at 90° of flexion without external rotation.
Figure 15:
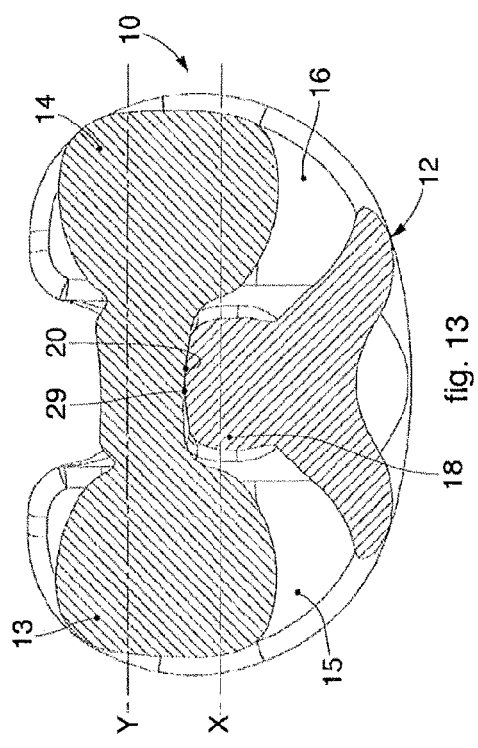
FIG. 15 is another section view from above of one form of embodiment of an artificial knee joint according to the present invention in a third functioning position at 90° of flexion with 6 degrees of external rotation.
Figure 16:
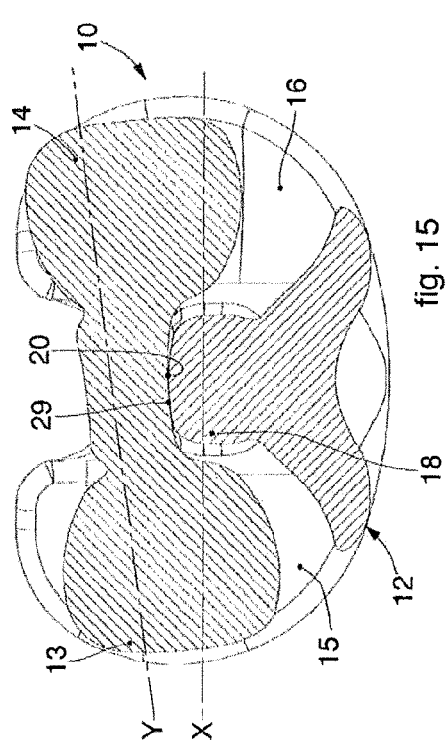
FIG. 16 is another section view from above of one form of embodiment of an artificial knee joint according to the present invention in a fourth functioning position at 90° of flexion with 6 degrees of external rotation.

In the configurations shown in FIGS. 13, 14, 15, the contact area remains on the rear surface 29 of the post 18 and the incongruent profile prevents stressing the edge of the post 18 with excessive loads.

In this way, no pressure is created on the edge of the post 18 that could damage it.

The rear position of the cam 17 in the femoral component 11 leads to a low point of contact, that is, directed toward the base surface 42, between cam 17 and post 18 for all the flexions of femur and tibia.

This is advantageous both because the section through the post 18, relating to the point of contact with the femoral cam 17, supplies suitable mechanical resistance but also because the contribution to said resistance also derives from the section through the complete tibial insert 12 (see FIGS. 11, 12). In fact, in correspondence with the point of contact, the area of the section is not only relative to the tibial post 18, but also to the front part of the tibial insert 12, achieving a bigger resistant surface.

Another advantageous aspect of the present invention is the direction of the force transmitted by the femoral cam 17 to the tibial post 18 during contact, which is directed downward and forward for all angles of flexion. The downward and forward direction of the force of contact reduces the risk of the tibial insert 12 detaching from the tibial plate to which it is attached mechanically during the implantation. This is because the downward direction of the force of contact generates a pressure that increases the stability of the coupling of the tibial insert 12 and tibial plate.

It is clear that modifications and/or additions of parts may be made to the artificial knee joint as described heretofore, without departing from the field and scope of the present invention.

It is also clear that, although the present invention has been described with reference to some specific examples, a person of skill in the art shall certainly be able to achieve many other equivalent forms of artificial knee joint, having the characteristics as set forth in the claims and hence all coming within the field of protection defined thereby.

The invention claimed is:

1. Artificial knee joint, comprising:
   a femoral component (11), able to be attached to a distal end of a femur, provided with a medial condyle (13), a lateral condyle (14) and a front flange (50), said medial condyle (13) and said lateral condyle (14) being joined together, in proximity with the rear end of an intercondyle groove (19), by a femoral cam (17) asymmetrical with respect to a central plane (α) of said femoral component (11) and comprising a distal surface (20) shaped like a drum which articulates with a tibial post (18), and separated by said intercondyle groove (19) in the remaining part of their extension;

a tibial component suitable to be attached to a proximal end of a tibia, comprising a tibial plate and a tibial insert (12), said tibial insert (12) being provided with a medial articulation surface (15) to support said medial condyle (13), and with a lateral articulation surface (16) to support said lateral condyle (14), and with said tibial post (18) substantially symmetrical with respect to a central plane (δ) of said tibial insert (12), wherein said tibial post (18) and said femoral cam (17) define a point of contact on which a direct force transmitted by the femoral cam (17) to the tibial post (18) is exerted along an axis of application (Z), said force having a direction downward and forward, and wherein a contact profile between the post (18) and the cam (17), for different angles of rotation of femur and tibia, is complementary in correspondence with a central contact point to prevent stressing the edge of said post (18) with excessive loads; wherein said femoral cam (17) has a concavity defined by an arc (A) with a radius (R1) along an axis (Y) perpendicular to a central femoral plane (a); and wherein said tibial post (18) comprises a rear surface (29) having a radius (R2), lying on a plane parallel to a base surface (42) of said tibial insert (12), which is substantially half said radius (R1) of said arc (A).

2. Artificial knee joint as in claim 1, wherein a center of said distal surface (20) is nearer to the medial condyle (13) than to the lateral condyle (14), resulting in a maximum medial diameter smaller than the maximum lateral diameter of said distal surface (20).

3. Artificial knee joint as in claim 1, wherein a ratio between the radius (R3) of sagittal curvature of the tibial post (18) and a radius (R4) of sagittal curvature of the femoral cam (17) has values comprised between 10% and 50%.

4. Artificial knee joint as in claim 1, wherein a front surface (36) of the tibial post (18) is substantially congruent with the front end (37) of the intercondyle groove (19) of the femoral component (11).

* * * * *